(12) United States Patent
Tanishiki

(10) Patent No.: US 7,798,002 B2
(45) Date of Patent: Sep. 21, 2010

(54) AUTOMATIC ULTRASONIC EXAMINATION DEVICE, AUTOMATIC ULTRASONIC EXAMINATION METHOD AND PRODUCTION METHOD USING THE EXAMINATION METHOD

(75) Inventor: Hideki Tanishiki, Osaka (JP)

(73) Assignee: Exedy Corporation, Osaka (JP)

( * ) Notice: Subject to any disclaimer, the term of this patent is extended or adjusted under 35 U.S.C. 154(b) by 391 days.

(21) Appl. No.: 11/884,197

(22) PCT Filed: Feb. 9, 2006

(86) PCT No.: PCT/JP2006/302233

§ 371 (c)(1), (2), (4) Date: Aug. 13, 2007

(87) PCT Pub. No.: WO2006/085570

PCT Pub. Date: Aug. 17, 2006

(65) Prior Publication Data

US 2008/0210009 A1 Sep. 4, 2008

(30) Foreign Application Priority Data

Feb. 14, 2005 (JP) .............................. 2005-036202

(51) Int. Cl.
 *G01N 29/265* (2006.01)
(52) U.S. Cl. .............................. 73/620; 73/618; 73/619
(58) Field of Classification Search .................... 73/618, 73/619, 620
 See application file for complete search history.

(56) References Cited

U.S. PATENT DOCUMENTS

| | | | | |
|---|---|---|---|---|
| 4,368,644 A | * | 1/1983 | Wentzell et al. | ................ 73/634 |
| 5,335,547 A | * | 8/1994 | Nakajima et al. | .............. 73/622 |
| 5,583,292 A | * | 12/1996 | Karbach et al. | ............... 73/638 |
| 5,773,721 A | * | 6/1998 | Bashyam | ...................... 73/596 |
| 2007/0144262 A1 | * | 6/2007 | Aznar et al. | ................... 73/633 |

FOREIGN PATENT DOCUMENTS

| | | | |
|---|---|---|---|
| DE | 10125782 A1 | * | 3/2003 |
| DE | 102005043699 | * | 3/2007 |
| DE | 102005043776 | * | 3/2007 |
| JP | 61-048360 U | | 4/1986 |
| JP | 63-148864 U | | 9/1988 |
| JP | 05-288724 A | | 11/1993 |
| JP | 06-265529 A | | 9/1994 |
| JP | 08-110332 A | | 4/1996 |
| JP | 11-326287 A | | 11/1999 |
| JP | 2002-098674 A | | 4/2002 |
| JP | 2006-153710 A | | 6/2006 |

* cited by examiner

*Primary Examiner*—Hezron Williams
*Assistant Examiner*—Nashmiya Fayyaz
(74) *Attorney, Agent, or Firm*—Global IP Counselors, LLP

(57) ABSTRACT

An automatic ultrasonic examination device includes an ultrasonic test instrument, a robot arm, and a control device. The ultrasonic test instrument includes an ultrasonic probe to send ultrasonic and detecting reflected waves while being in contact with the spot-welded portion, and an ultrasonic test instrument main device connected to the ultrasonic probe to convert the reflected wave detection signals received from the ultrasonic probe into test information. The control device includes a real center location computing unit to identify a real center location of the spot-welded portion with reference to pieces of test information obtained around a preset tentative center location of the spot-welded portion, and a determination unit to check quality of the spot-welded portion with reference to test information obtained at the real center location.

13 Claims, 10 Drawing Sheets

AUTOMATIC ULTRASONIC EXAMINATION DEVICE, AUTOMATIC ULTRASONIC EXAMINATION METHOD AND PRODUCTION METHOD USING THE EXAMINATION METHOD

BACKGROUND OF THE INVENTION

1. Technical Field

The present invention relates to automatic ultrasonic examination devices, automatic ultrasonic examination methods and production methods using the examination method. The invention particularly relates to automatic ones using robots.

2. Background Art

It has been conventionally known that there is a method using ultrasonic test instruments as nondestructive examination methods for inspecting spot-welded portions. The ultrasonic test instrument includes, for example, an ultrasonic probe for sending ultrasonic waves and detecting the reflected waves while being in contact with spot-welded portions, and an ultrasonic test instrument main device connected to the ultrasonic probe for receiving reflected wave detection signals from the ultrasonic probe and converting them into test data. In the ultrasonic test instrument, since ultrasonic waves are attenuated through a nugget formed inside of the spot-welded portion, it is possible to check quality of the welded portions, as shown in Japanese Unexamined Patent Publication H11-326287

PROBLEMS TO BE SOLVED BY THE INVENTION

In order to test precisely the spot-welded portions, it is necessary for the ultrasonic probe to contact the center location of the nugget for an ultrasonic test. However, the precise center location of the nugget is different from the apparent center location of weld scars in many cases, so that it is difficult to identify the precise center location from the appearance. Even if the precise center location is identified, since levels of the reflected waves relative to the nugget are different depending on incident angles of the ultrasonic waves, it is difficult to check precisely the quality of the spot-welded portions and troublesome to adjust the angle of the ultrasonic probe. Especially if the spot-welded portion is formed on a curved surface, it consumes a lot of working hours. Accordingly, if an operator performs a test operation, the accuracy of the quality check and the operation efficiency are extremely deteriorated.

Alternatively, although an apparatus has been proposed that performs the test operation by robots, no method of the operation has been proposed to identify the center location of the nugget in the spot-welded portions or to adjust the optimum incident angle of the ultrasonic waves efficiently and highly accurately.

SUMMARY OF THE INVENTION

It is an object of the present invention to check quality of spot-welded portions using an ultrasonic test instrument highly accurately and at high speed.

Unit for Solving Problems

An automatic ultrasonic examination device according to a first aspect of the present invention is provided to test automatically a spot-welded portion of a test object. The device includes an ultrasonic test instrument, a robot arm, and a control device. The ultrasonic test instrument includes an ultrasonic probe to send ultrasonic waves and detecting reflected waves while being in contact with the spot-welded portion and an ultrasonic test instrument main device connected to the ultrasonic probe to convert the reflected wave detection signals received from the ultrasonic probe into test information. The robot arm includes a plurality of joints to adjust three-dimensionally the posture and location of the ultrasonic probe relative to the spot-welded portion. The control device is connected to the ultrasonic test instrument and robot arm to communicate data and signals with the ultrasonic test instrument and robot arm. The control device includes a real center location identifying unit to identify a real center location of the spot-welded portion with reference to pieces of test information obtained around a preset tentative center location of the spot-welded portion, and a determination unit to check quality of the spot-welded portion with reference to the test information obtained at the real center location.

In the automatic ultrasonic examination device, since the real center location identifying unit can identify the real center location of the spot-welded portion, i.e., the center location of a nugget that cannot be judged from the appearance, it is possible to check quality of the spot-welded portions with a high degree of accuracy compared to the operation by the operator. In addition, the automatic operation by the control device and robot arm makes it possible to perform the operation at high speed compared to the operation by the operator.

An automatic ultrasonic examination device according to a second aspect of the present invention is the device of the first aspect, wherein the control device further includes an optimum test information unit to obtain test information optimum to check quality of the spot-welded portion with reference to pieces of test information obtained around the central axis of the real center location while pivoting on a contact point between the ultrasonic probe and the real center location. The determination unit checks the quality of the spot-welded portion with reference to the optimum test information.

In the automatic ultrasonic examination device, since the determination unit checks the quality with reference to the optimum test information, it is possible for the determination unit to check the quality with a high degree of accuracy.

An automatic ultrasonic examination device according to a third aspect of the present invention is the device of the first or second aspect, wherein the location and number of the test points can be preset by the control device.

In the automatic ultrasonic examination device, since locations and number of the test points can be preset, it is possible to deal with various spot-welded portions in size.

An automatic ultrasonic examination device according to a fourth aspect of the present invention is the device of any of the first to third aspects, wherein a space between the adjacent test points can be preset by the control device.

In the automatic ultrasonic examination device, since a space between the adjacent test points can be preset, it is possible to deal with various spot-welded portions in size.

An automatic ultrasonic examination device according to a fifth aspect of the present invention is the device of any of the first to fourth aspects, wherein the test points are located around the tentative center location in a lattice arrangement.

In the automatic ultrasonic examination device, since the test points are located in a lattice arrangement, it is possible to identify more precisely the real center location.

An automatic ultrasonic examination device according to a sixth aspect of the present invention is the device of any of the first to fifth aspects. The device further includes a tentative center location identifying unit connected to the control device to identify a tentative center location by taking in and image processing the image data of the spot-welded portion.

In the automatic ultrasonic examination device, since the tentative center location identifying unit identifies the tentative center location judged from the appearance, it is possible to identify the tentative center location close to the real center location, thereby reducing the number of pieces of the test information obtained by the real center location identifying unit. As a result, it is possible to check quality of the spot-welded portion with a high degree of accuracy at high speed.

An automatic ultrasonic examination method according to a seventh aspect of the present invention to test automatically a spot-welded portion of a test object, in an automatic ultrasonic examination device including an ultrasonic test instrument to obtain test information from the test object, and a robot arm to adjust three-dimensionally the posture and position of the ultrasonic test instrument relative to the test object, is provided. The method includes a real center location identifying step to identify a real center location of the spot-welded portion with reference to pieces of the test information around a tentative center location of the spot-welded portion obtained by the ultrasonic test instrument, and a determination step to check the quality of the spot-welded portion with reference to the test information obtained at the real center location.

In the automatic ultrasonic test method, since the real center location identifying step is included, it is possible to check the quality of the spot-welded portion with a high degree of accuracy compared to the operation by the operator.

An automatic ultrasonic examination method according to an eighth aspect of the present invention is the method of seventh aspect, and further includes an optimum test information detection step to obtain test information optimum to check the quality of the spot-welded portion with reference to pieces of test information obtained around the central axis of the real center location while pivoting on a contact point between the ultrasonic probe and the real center location. In the determination step, the quality of the spot-welded portion is checked with reference to the optimum test information.

In the automatic ultrasonic test method, since the quality is checked with reference to the optimum test information, it is possible to check the quality of the spot-welded portion with a high degree of accuracy.

An automatic ultrasonic examination method according to a ninth aspect of the present invention is the method according to the seventh or eighth aspect is provided. The method further includes a tentative center location identifying step to identify the tentative center location by image-processing the image data of the spot-welded portion.

In the automatic ultrasonic test method, since the tentative center location can be identified according to the appearance of the spot-welded portion, it is possible to reduce the number of pieces of the test information obtained at the real center location identifying step. As a result, it is possible to check the quality of the spot-welded portion with a high degree of accuracy and to perform the operation at high speed.

A method of producing spot-welded products according to a tenth aspect includes a spot welding step to spot-weld a plurality of metal materials, and an ultrasonic test step to check the quality of the welded portion of the spot-welded product using an ultrasonic examination method according to any of the seventh to ninth aspects.

In the production method, since quality of the welded portion is checked using the automatic ultrasonic examination method as recited in any of the seventh to ninth aspects, it is possible to check the quality of the welded portion with a high degree of accuracy at high speed, as well as improving quality and productivity of the spot-welded product, compared to the operation by the operator.

Effect of the Invention

In the automatic ultrasonic examination device and the examination method according to the present invention, the identification of the center location of the nugget and the estimate of the test points performed as described above make it possible to perform the test with a high degree of accuracy at high speed.

In the production method according to the present invention, use of the automatic ultrasonic examination method makes it possible to improve quality and productivity of the spot-welded product.

DETAILED DESCRIPTION OF THE PREFERRED EMBODIMENTS

A detailed description will be made on one embodiment of the present invention referring to the figures.

Structure of the Automatic Ultrasonic Examination Device

Figure 1:
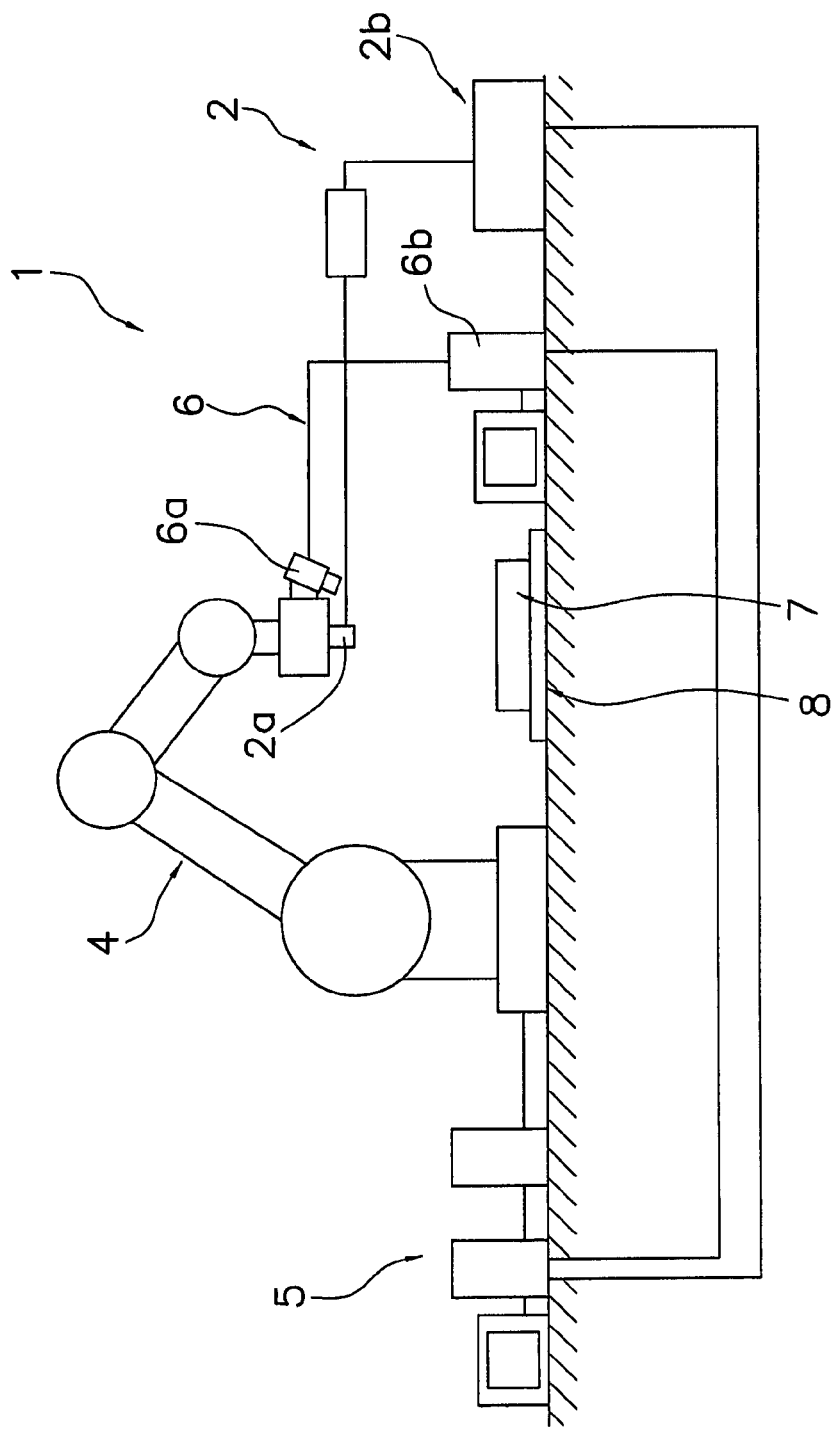
FIG. 1 is a view of an entire arrangement of an automatic ultrasonic examination device according to one embodiment of the present invention.
Figure 2:
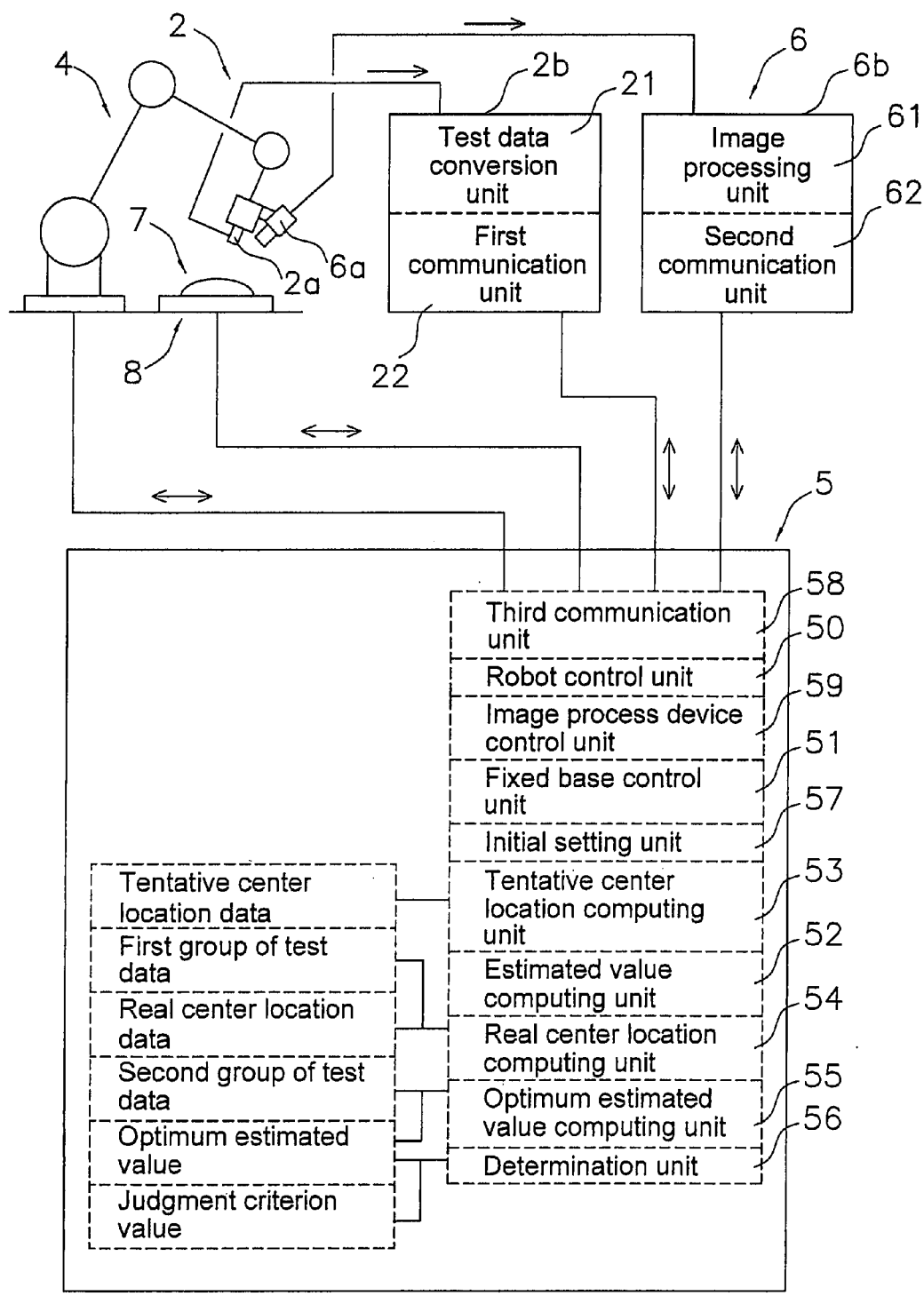
FIG. 2 is a detailed structure view of the automatic ultrasonic examination device of the one embodiment of the present invention.

FIG. 1 shows a view of an entire arrangement of an automatic ultrasonic examination device of one embodiment of the present invention, and FIG. 2 shows a detailed structure view of an automatic ultrasonic examination device of the one embodiment of the present invention. An automatic ultrasonic examination device 1 serves to test automatically spot-welded portions of a test object 7, and includes an ultrasonic test instrument 2, robot arms 4, a tentative center location identifying device 6 (tentative center location identifying unit), a fixed base 8, and a control deice 5.

Ultrasonic Test Instrument 2

The ultrasonic test instrument 2 serves to test the spot-welded portions by ultrasonic waves, and includes an ultrasonic probe 2a and an ultrasonic test instrument main device 2b. The ultrasonic probe 2a serves to send ultrasonic waves and to detect reflected waves while being in contact with the spot-welded portions, and is attached to the tip of the robot arm 4. The ultrasonic probe 2a is connected to the ultrasonic test instrument main device 2b so that it can send reflected wave detection signals to the ultrasonic test instrument main device 2b. The ultrasonic test instrument main device 2b serves to receive the reflected wave detection signals from the ultrasonic probe 2a, and to convert the reflected wave detection signals into test data. The device 2b is connected to the ultrasonic probe 2a.

As an example of the ultrasonic test instrument main device 2b, a personal computer or the like can be employed that is provided with a CPU, RAM, and ROM. As shown in FIG. 2, software applications that are pre-installed in the ultrasonic test instrument main device 2b realize a test data conversion unit 21 and a first communication unit 22. The test data conversion unit 21 has a function of receiving the reflected wave detection signals from the ultrasonic probe 2a and converting them into the test data. The first communication unit 22 has a function of communicating with the control device 5 (described later). It should be noted that "the test data" unit data are composed of the travel of the ultrasonic waves and the level of the reflected waves.

(2) Robot Arm 4

The robot arm 4 serves to adjust three-dimensionally the posture and location of the ultrasonic probe 2a relative to the spot-welded portions. The robot arm 4 is provided with a plurality of joints so that it can move the ultrasonic probe 2a to any location according to instructions from a robot control unit 50 (described later) of the control device 5.

(3) Tentative Center Location Identifying Device 6

The tentative center location identifying device 6 serves to identify the tentative center location according to the appearance of the spot-welded portion, and includes a camera 6a and an image processing device 6b. The camera 6a is attached to the tip of the robot arm 4 where it does not interfere with the ultrasonic probe 2a. Additionally, the attachment location and angle of the camera 6a are adjusted so that the spot-welded portions can be shot when the tip of the ultrasonic probe 2a is in contact with the spot-welded portion.

One example of the image processing device 6b is a personal computer as in the case of the ultrasonic test instrument main device 2b. As shown in FIG. 2, software applications pre-installed in the image processing device 6b realize an image processing unit 61 and a second communication unit 62. The image processing unit 61 has a function of identifying the tentative center location of the spot-welded portion by image process. The second communication unit 62 has a function of communicating with the control device 5 (later described). The detail of functions of the image processing unit 61 will be described later.

(4) Fixed Base 8

The fixed base 8 serves to fix the test object 7 thereto, and is provided with positioning pins or the like depending on the test object 7. The fixed base 8 is configured to rotate and to move horizontally, the movements being controlled by the fixed base control unit 51 (described later) of the control device 5. In the control device 5, coordinates in three axial directions (X axis, Y axis, Z axis) are preset using the center coordinate and the center of the fixed base 8. Accordingly, if the location of the spot-welded portion in the test object 7 is known, the control device 5 can set position coordinates of the spot-welded portions from the center of the fixed base 8, thereby moving the ultrasonic probe 2a to a rough center location (an initial center location) of the spot-welded portion.

Figure 3:
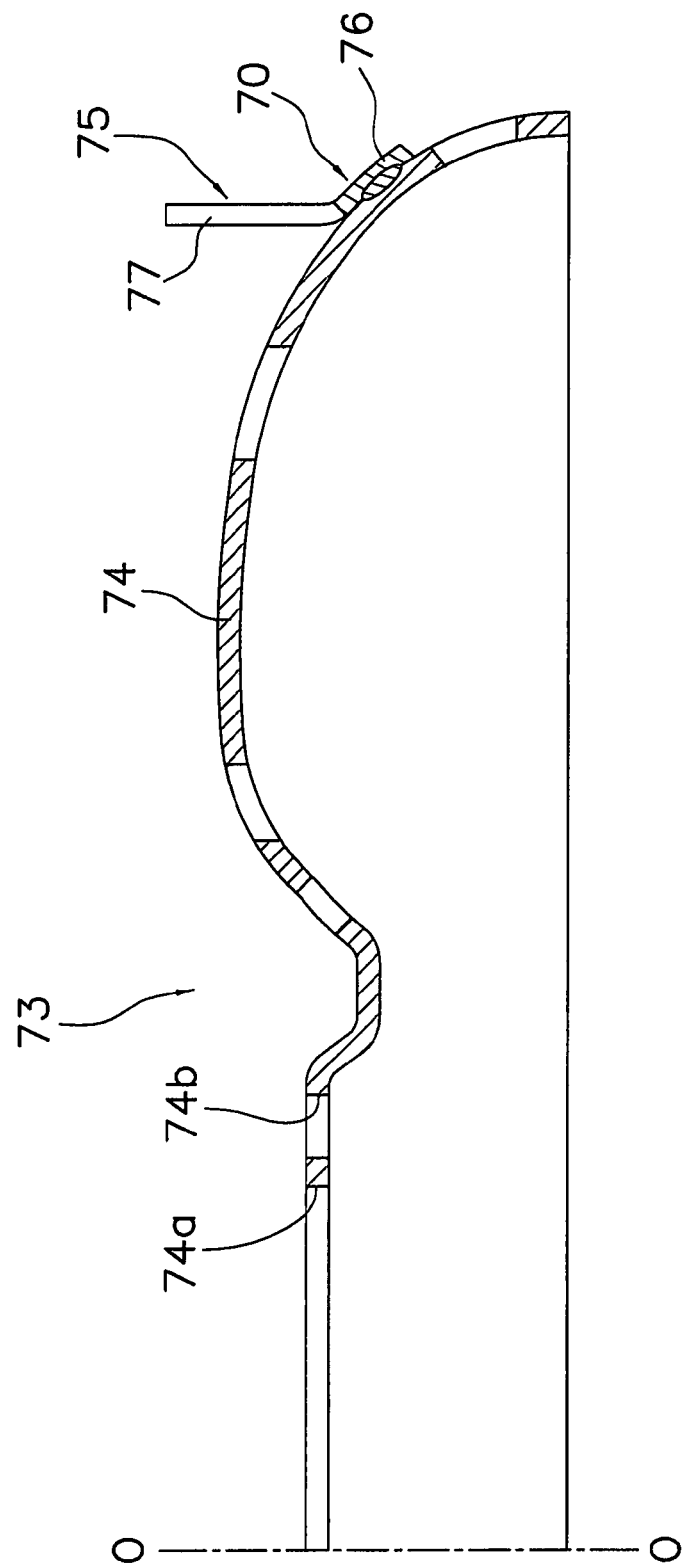
FIG. 3 is a cross-sectional view of the turbine shell 73 as a test object 7.

In the present embodiment, as the test object 7, a turbine shell 73 for a torque converter will be described. FIG. 3 shows a cross-sectional view of the turbine shell 73. O-O in FIG. 3 represents the rotational axis of the torque converter. The turbine shell 73 is constituted by an annular shell body 74 and a driven plate 75. The driven plate 75 is constituted by an annular portion 76 and a plurality of projections 77 projecting in an axial direction from a radially inner portion of the annular portion 76. The annular portion 76 is fixed to the surface of the radially outer portion of the shell body 74 by spot welding so that the turbine shell 73 is formed with a plurality of spot-welded portions 70. The automatic ultrasonic examination device 1 of the present embodiment tests the spot-welded portions 70 by ultrasonic waves.

(5) Control Device 5

The control device 5 serves to control the automatic ultrasonic examination device 1 so as to perform automatically the test operation, and can send and receive data and signals between itself and peripheral devices. One example of the control device 5 is a personal computer as in the case of the ultrasonic test instrument main device 2b. As shown in FIG. 2, software applications preinstalled in the control device 5 realize a robot control unit 50, a fixed base control unit 51, an estimated value computing unit 52, a tentative center location computing unit 53, a real center location computing unit 54, an optimum estimated value computing unit 55, a determination unit 56, an initial setting unit 57, a third communication unit 58, and an image processing device control unit 59.

The robot control unit 50 has a function of controlling the movement of the robot arm 4. The fixed base control unit 51 has a function of controlling the movement of the fixed base 8. The estimated value computing unit 52 has a function of converting the test data obtained by the ultrasonic test instrument 2 into estimated values. The tentative center location computing unit 53 has a function of calculating the coordinate of the tentative center location data, the data being obtained by the tentative center location identifying device 6.

The real center location computing unit 54 (a real center location identifying unit) has a function of identifying the real center location of the spot-welded portion according to a plurality of estimated values around the tentative center location. The optimum estimated value computing unit 55 has a function of obtaining an estimated value to check the quality according to a plurality of estimated values gained by changing angles of the ultrasonic probe 2a at the real center location. The determination unit 56 has a function of checking the quality of the spot-welded portions according to the optimum estimated value gained by the optimum estimated value computing unit 55.

The initial setting unit 57 has a function of presetting numerical values to be necessitated by each of the computing units. The third communication unit 58 connects the units with each other, and has a function of communicating with the peripheral devices. The image processing device control unit 59 has a function of sending an image processing instruction to the image processing unit 61. Detail of functions of each unit will be described later.

2. Operation Flow of the Automatic Ultrasonic Examination Device

Figure 4:
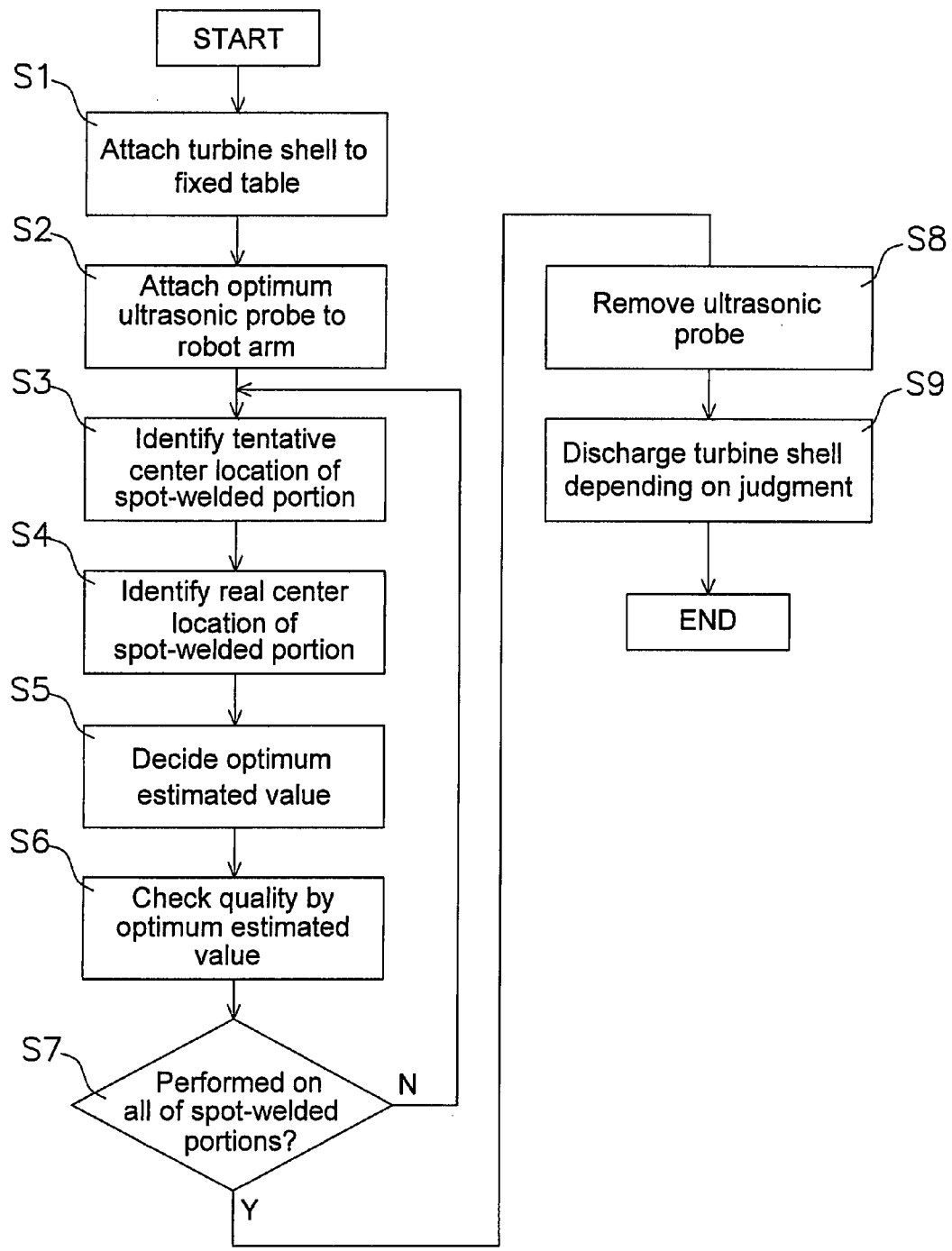
FIG. 4 is a view of one example of the operation flow using the automatic ultrasonic examination device 1 of the one embodiment of the present invention.

FIG. 4 shows one example of the operation flow of the automatic ultrasonic examination device 1 of one embodiment of the present invention. As shown in FIG. 4, the operation flow of the automatic ultrasonic examination device 1 is mainly made of steps from first step S1 to ninth step S9.

(1) First step S1

At first step S1, the turbine shell 73 is attached to the fixed base 8 by the robot arm 4, while the ultrasonic probe 2a is not attached to the tip of the robot arm 4. This step needs not to be performed by the robot arm 4 of the automatic ultrasonic examination device 1 in a case that a robot of adjacent apparatus performs the operation.

(2) Second step S2

The optimum diameter of the ultrasonic probe 2a varies depending on the diameter of spot-welded portions. At the second step S2, the robot arm 4 selects the optimum ultrasonic probe 2a. This is preset by the initial setting unit 57 of the control device 5 depending on types of the test object 7. If first step S1 is implemented by the robot of the adjacent apparatus, this step can be omitted except for a case in which types of the test object 7 is changed.

(3) Third Step S3 (Tentative Center Location Identifying Step)

At the third step S3, the tentative center location is identified by the tentative center location identifying device 6 according to the appearance of the spot-welded portion. The center location of the spot-welded portions will be described herein.

Figure 5:
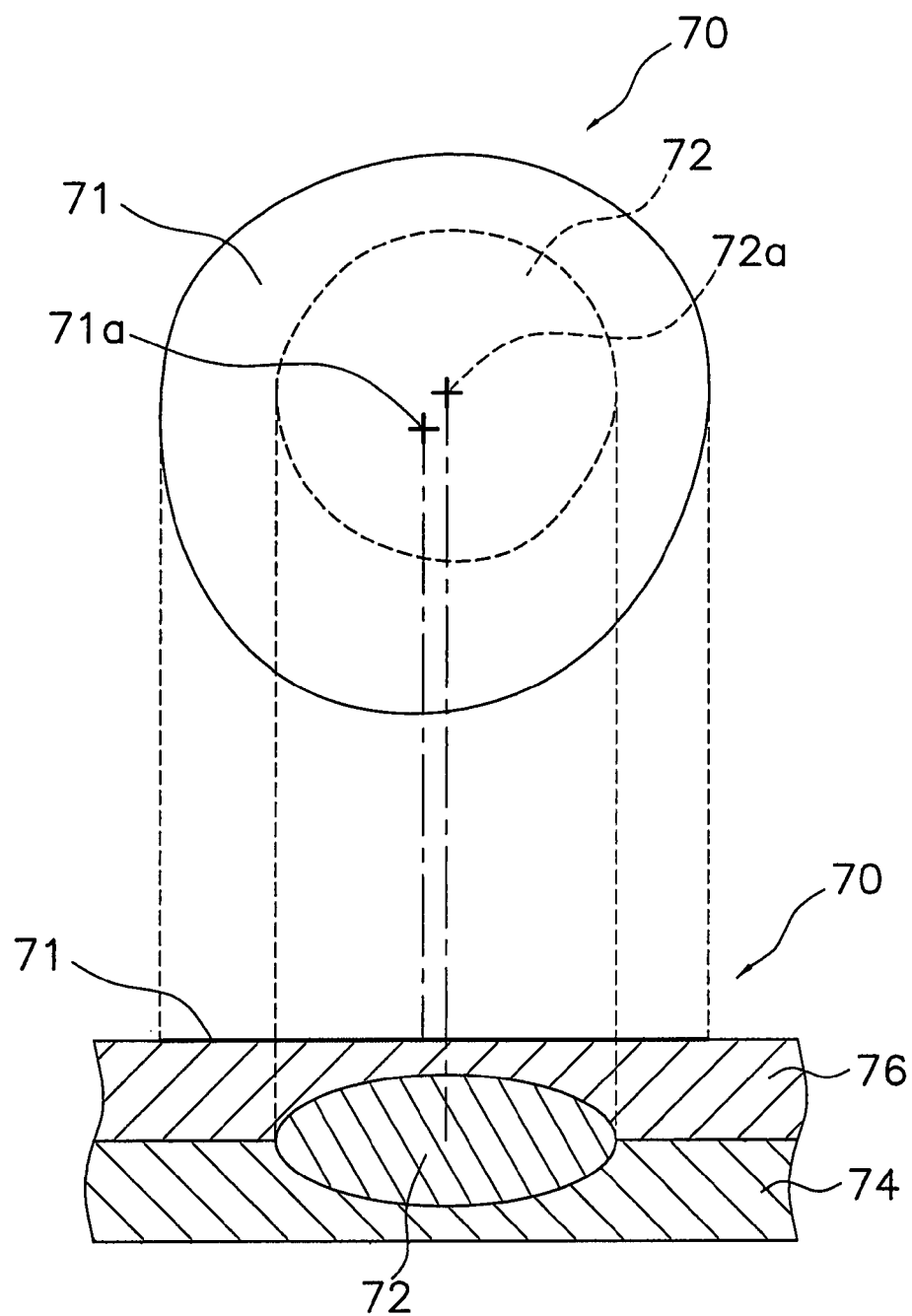
FIG. 5 is a cross-sectional view and plan view of the spot-welded portions 70.

FIG. 5 shows a cross sectional view and plan view of the spot-welded portion 70. As shown in FIG. 5, the spot-welded portion 70 is formed with a distorted circular scar such as a weld scar 71. Meanwhile, a nugget 72 is formed between the driven plate 75 and the annular portion 76 by spot welding. The nugget 72 is a portion where the driven plate 75 and the annular portion 76 are welded to each other.

The weld scar 71 and the nugget 72 have a circular shape with a small amount of distortion in the plan view. If it is assumed that the center location of the weld scar 71 is an appearance center location 71a and the center location of the nugget 72 is an inner center location 72a, both the center locations 71a and 72a do not generally correspond to each other as shown in FIG. 5. Meanwhile, in order to check precisely the quality of the spot-welded portion 70, it is preferable to test the inner center location 72a of the nugget 72.

Figure 6:
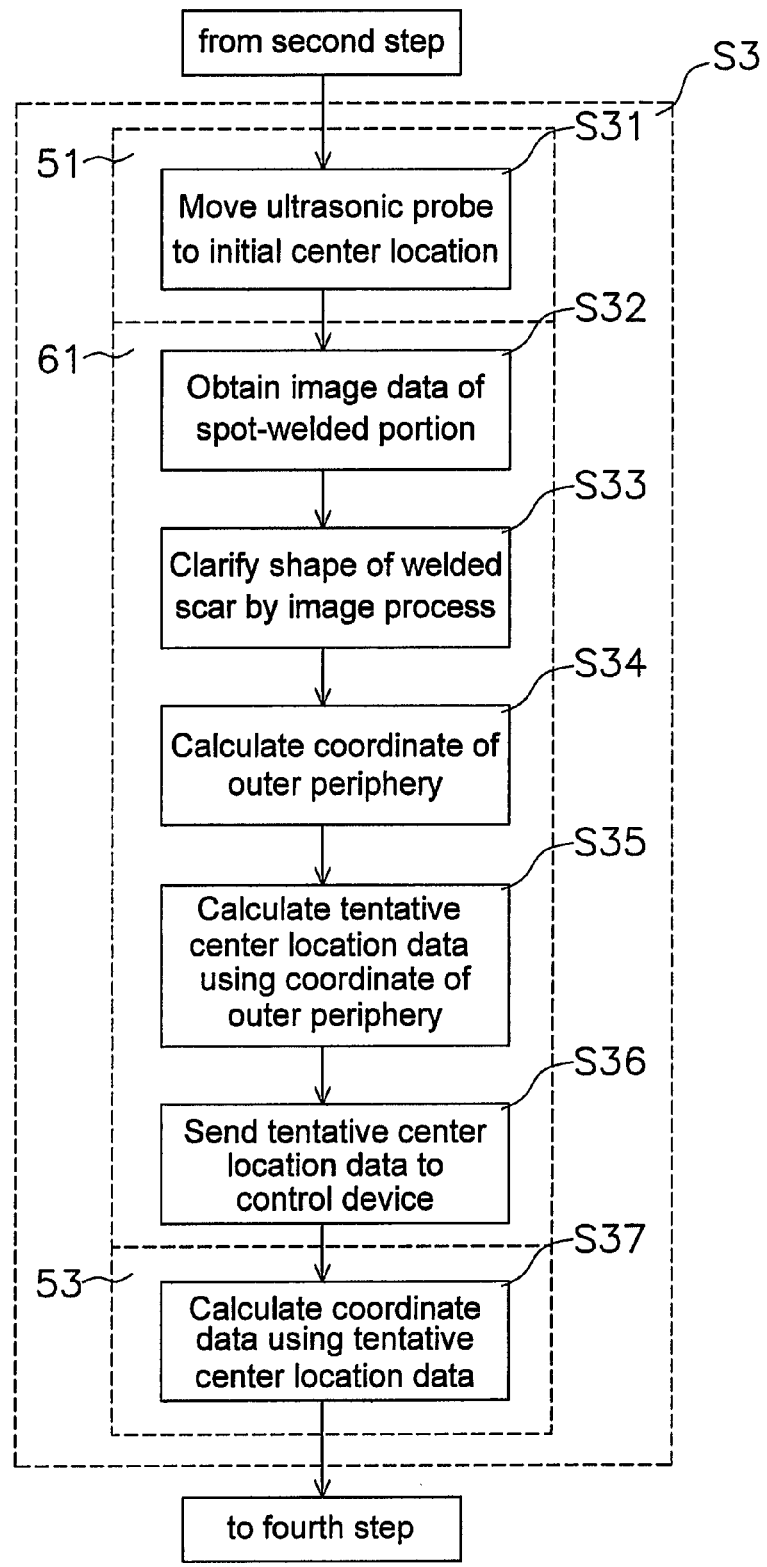
FIG. 6 is a detailed flow chart of the third step S3.

At this step, according to the flow diagram shown in FIG. 6, first, the tentative center location equivalent to the appearance center location 71a is identified by the tentative center location identifying device 6 according to the appearance. This will makes it easier to identify the inner center location 72a.

First, the robot control unit 50 sends an instruction to the robot arm 4, and then the robot arm 4 moves the ultrasonic probe 2a to the initial center location of the spot-welded portion (step S31). Then, the tip of the ultrasonic probe 2a is brought into contact with the initial center location. As a result, the camera 6a, which is attached to the tip of the robot arm 4, makes it possible to shoot the spot-welded portion.

Next, the image processing device control unit 59 of the control device 5 sends a shooting instruction to the image processing device 6b, and the image data of the spot-welded portions 70 are obtained by the image processing unit 61 (step S32). Then, the obtained image data are subjected to image processing such that the shape of the weld scar 71 of the spot-welded portions 70 becomes clearer (step S33). Specifically, the image processing device 6b performs the image processing by making use of the differences in brightness and color between the weld scar 71 and the peripheral portion such that the coordinate of the outside shape can be calculated, thereby figuring out the shape of the weld scar 71.

Finally, the coordinate of the outer periphery of the weld scar 71 on the image data are calculated (step S34), the coordinate of the tentative center location on the image data are calculated using the coordinate of the outer periphery (step S35). After that, the tentative center location data are sent to the control device 5 (step S36).

The tentative center location computing unit 53 of the control device 5 calculates the coordinate data of the tentative center location on the coordinate provided on the fixed base 8, using the initial center location on the image data that is preset by the initial setting unit 57 and the obtained tentative center location data. The coordinate of the calculated tentative center location is stored into the control device 5.

As mentioned above, at third step S3, it is possible to obtain the coordinate data of the tentative center location of the spot-welded portions 70 in the coordinate provided on the fixed base 8.

(4) Fourth Step S4 (Real Center Location Identifying Step)

At the fourth step S4, a plurality of test data is obtained with reference to the tentative center location identified at the third step S3, and the real center location, which corresponds to the inner center location 72a of the spot-welded portions 70, is identified.

The method to identify the real center location will be described herein. As mentioned before, inside of the spot-welded portions 70 is formed the nugget 72 (refer to FIG. 5), which generally has the thickest portion in the center where the ultrasonic waves are most attenuated. Accordingly, as a way to identify the inner center location 72a of the nugget 72, it is assumed that among a plurality of points around a tentative center location 71b the point where the ultrasonic waves are most attenuated is the inner center location 72a (more precisely, the point closest to the inner center location 72a). At fifth step S5, as described above, the ultrasonic tests performed at a plurality of test points make it possible to identify the real center location.

Figure 7:
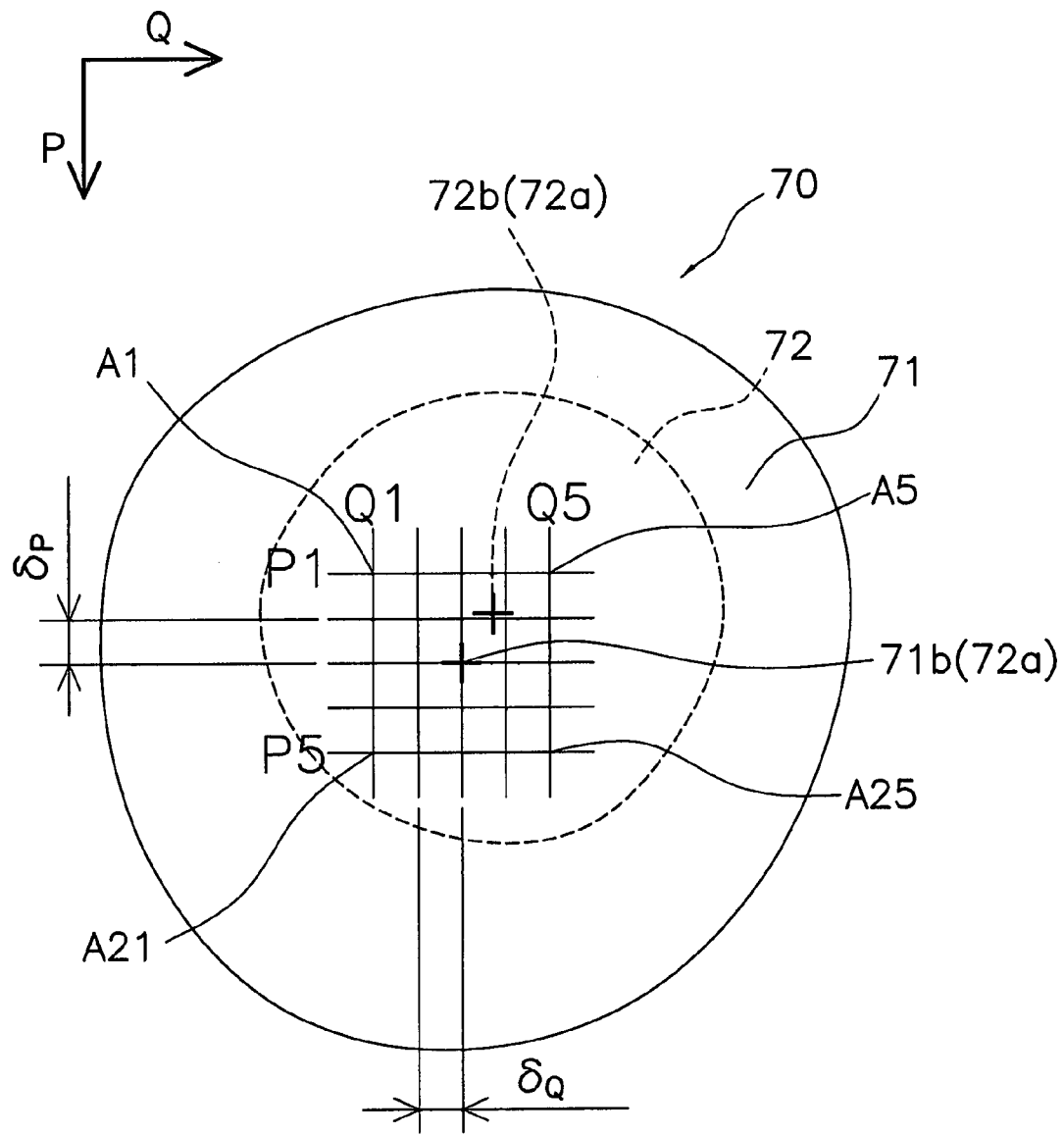
FIG. 7 is a view of one example of the positioning of the test points at the fourth step S4.
Figure 8:
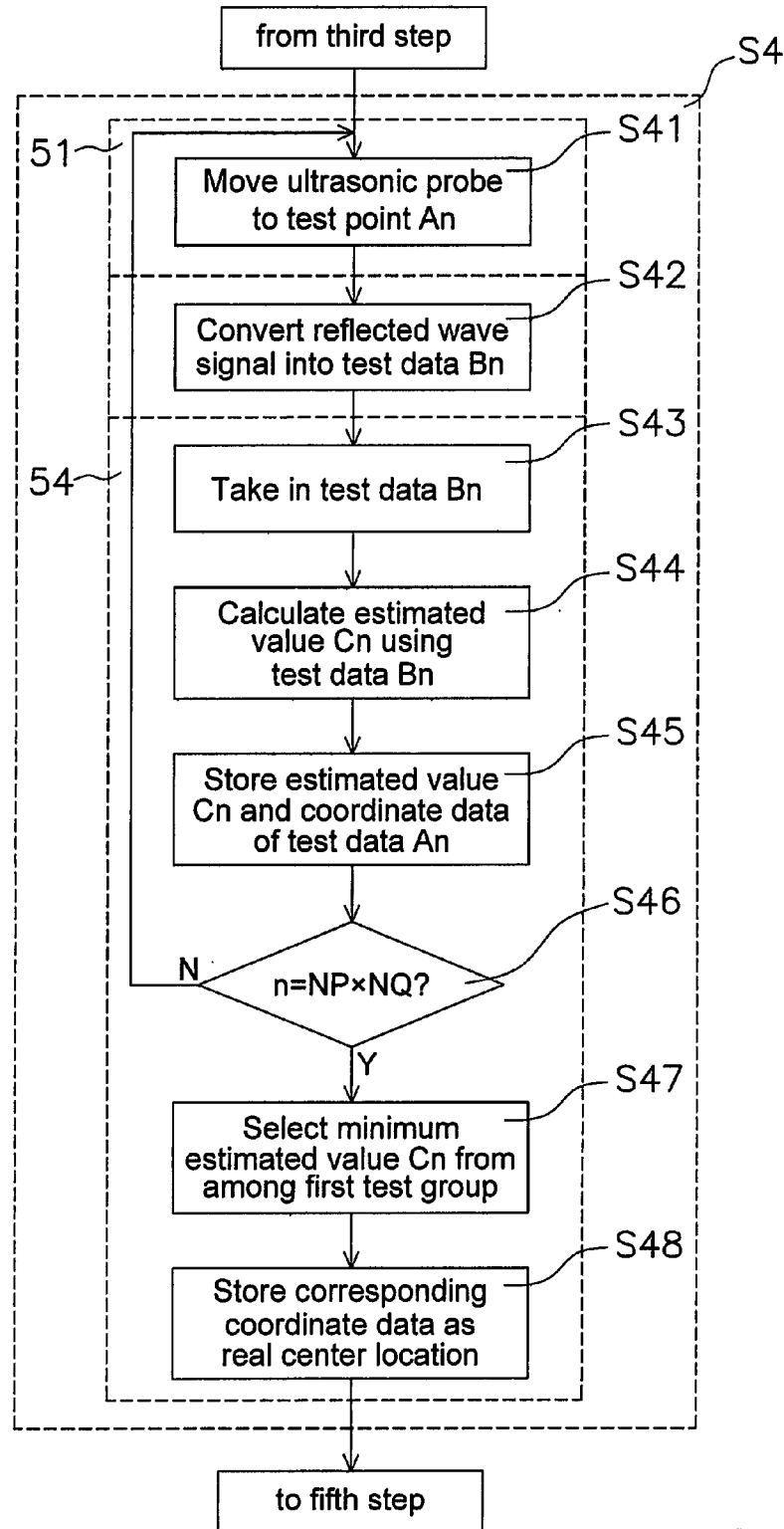
FIG. 8 is a detailed flow chart of the fourth step S4.

A more detailed description will be made on a plurality of test points. FIG. 7 shows one example of positioning of the test points at the fifth step. FIG. 7 is an enlarged view of a plan view of the spot-welded portion in FIG. 5. In FIG. 7, for convenience, the tentative center location 71b is represented as a point same as the point of the appearance center location 71a. As shown in FIG. 7, a flat surface is preset that includes the spot-welded portion 70 and P axis and Q axis intersecting with each other at right angles on the flat surface. The ultrasonic tests are performed at a plurality of test points $A_n$ disposed in a lattice-like arrangement along the directions of P axis and Q axis, where the number of points in the directions of P axis and Q axis are the number of the test points $N_P$ and $N_Q$, in this embodiment, a total of twenty five points (test points $A_1$ to $A_{25}$) are set by the control device 5, where $N_P=5$ and $N_Q=5$. In addition, a space between the adjacent test points in the directions of P axis and Q axis are preset by the control device 5 as test spaces $\delta_P$ and $\delta_Q$. At each of the test points set as described above, an ultrasonic test is carried out according to the flow diagram shown in FIG. 8.

First, the ultrasonic probe 2a is moved by the robot arm 4 to the test point $A_1$, so that the tip of the ultrasonic probe 2a is brought into contact with the test point $A_1$ (step S41). Next, the ultrasonic test instrument main device 2b obtains the test data with reference to the reflected wave detection signals sent from the ultrasonic probe 2a (step S42).

The test data $B_1$ at the test point $A_1$ which is obtained by the ultrasonic test instrument main device 2b are taken into the control device 5 (step S43). Then, the estimated value computing unit of the control device 5 calculates estimated value $C_1$ using the test data $B_1$ (step S44). In this embodiment, although "estimated value $C=2*N*t$" is employed that is calculated using the number of reflection echoes N and the measured plate thickness t, an estimated value that is calculated in another way can be employed. The calculated estimated value $C_1$ is stored into the control device 5 by the real center location computing unit of the control device 5 as first test data group as well as the coordinate data of the test point $A_1$ (step S45). Until the estimated value $C_1$ to $C_{25}$ at the test points $A_1$ to $A_{25}$ are obtained, the steps S41 to S45 are repeated (step S46). During this operation, angles of the ultrasonic probe 2a at each of the test points $A_n$ are the same as each other relative to the flat surface including P axis and Q axis, e.g., in perpendicular.

From among all of estimated values $C_1$ to $C_{25}$, the minimum estimated value is selected (step S47). Then, the coordinate data of the test points $A_n$ which correspond to the minimum estimated value $C_n$ are stored into the control device 5 as real center location data (step S48).

As described above, at the fourth step S4, it is possible to obtain the coordinate data of the real center location of the spot-welded portion.

(5) Fifth Step S5 (Optimum Test Information Detection Step)

At the fifth step S5, while the ultrasonic probe 2a is brought into contact with the real center location that is identified at the fifth step S5, a plurality of test data is obtained by changing the angle of the ultrasonic probe 2a, thereby to select test data that are optimum to check the quality of the spot-welded portion from among the test data.

Figure 9:
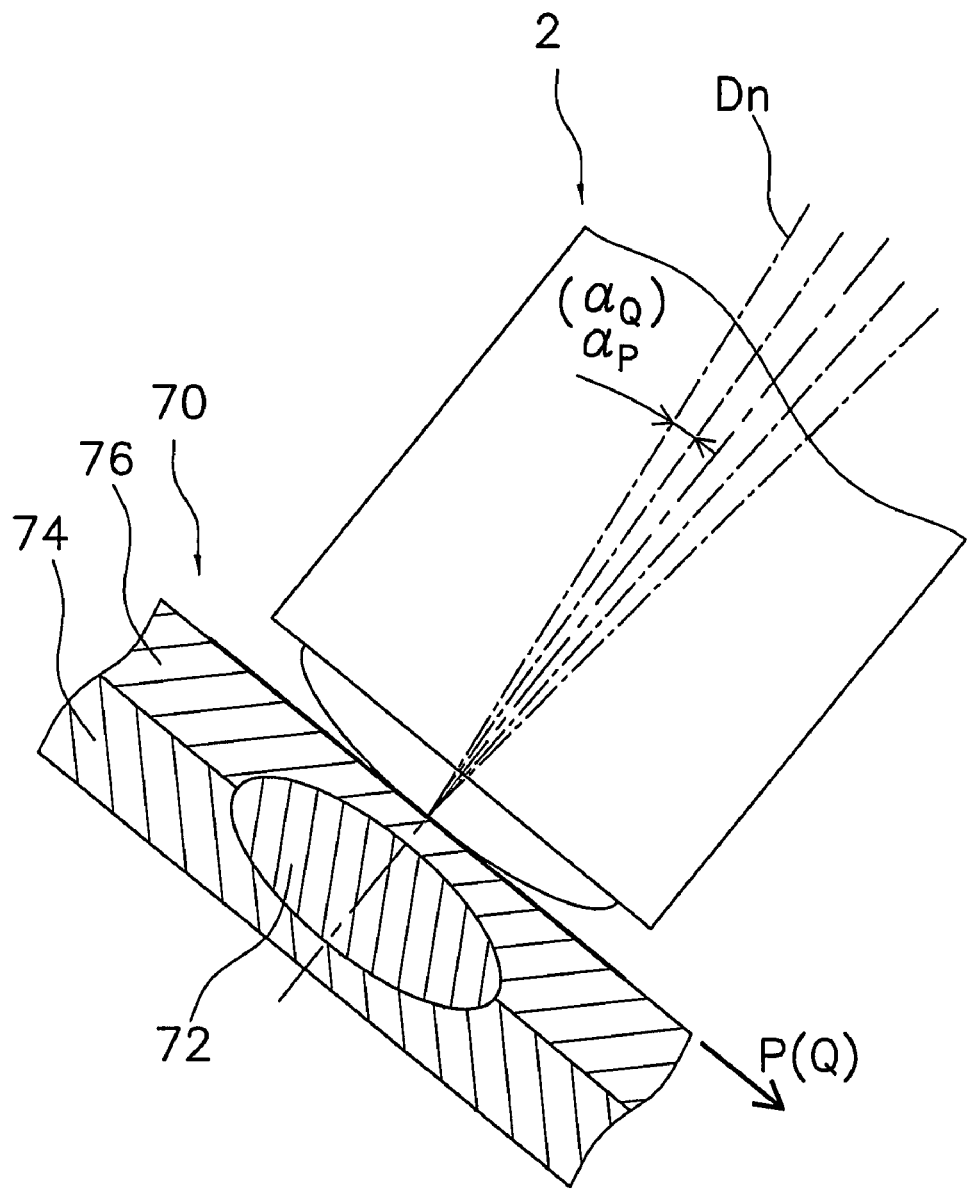
FIG. 9 is a view of one example of the setting of the test axis of the fifth step S5.

A description will be made on a way to obtain the optimum estimated value herein. FIG. 9 shows angle setting of the ultrasonic probe 2a at the fifth step S5. The angle of the ultrasonic probe 2a relative to the spot-welded portion at the initial state is perpendicular to the flat surface defined by the P axis and Q axis. Around the locations of the axes, the tests are performed along a plurality of test axes $D_n$ that have different angles against the directions of the P axis and Q axis. In the present embodiment, the number of the test axes Mp, $M_Q$ as the number of axes that are set in the directions of P axis and Q axis is set to be a total of twenty five points by the initial setting unit 57, where $M_P$=5 and $M_Q$=5. In addition, the angle between the adjacent test axes $D_n$ in the directions of P axis and Q axis is preset by the initial setting unit 57 as test angles $\alpha_P$ and $\alpha_Q$. Along each of test axes $D_n$ set as described above, the ultrasonic test is performed as described hereinafter.

Figure 10:
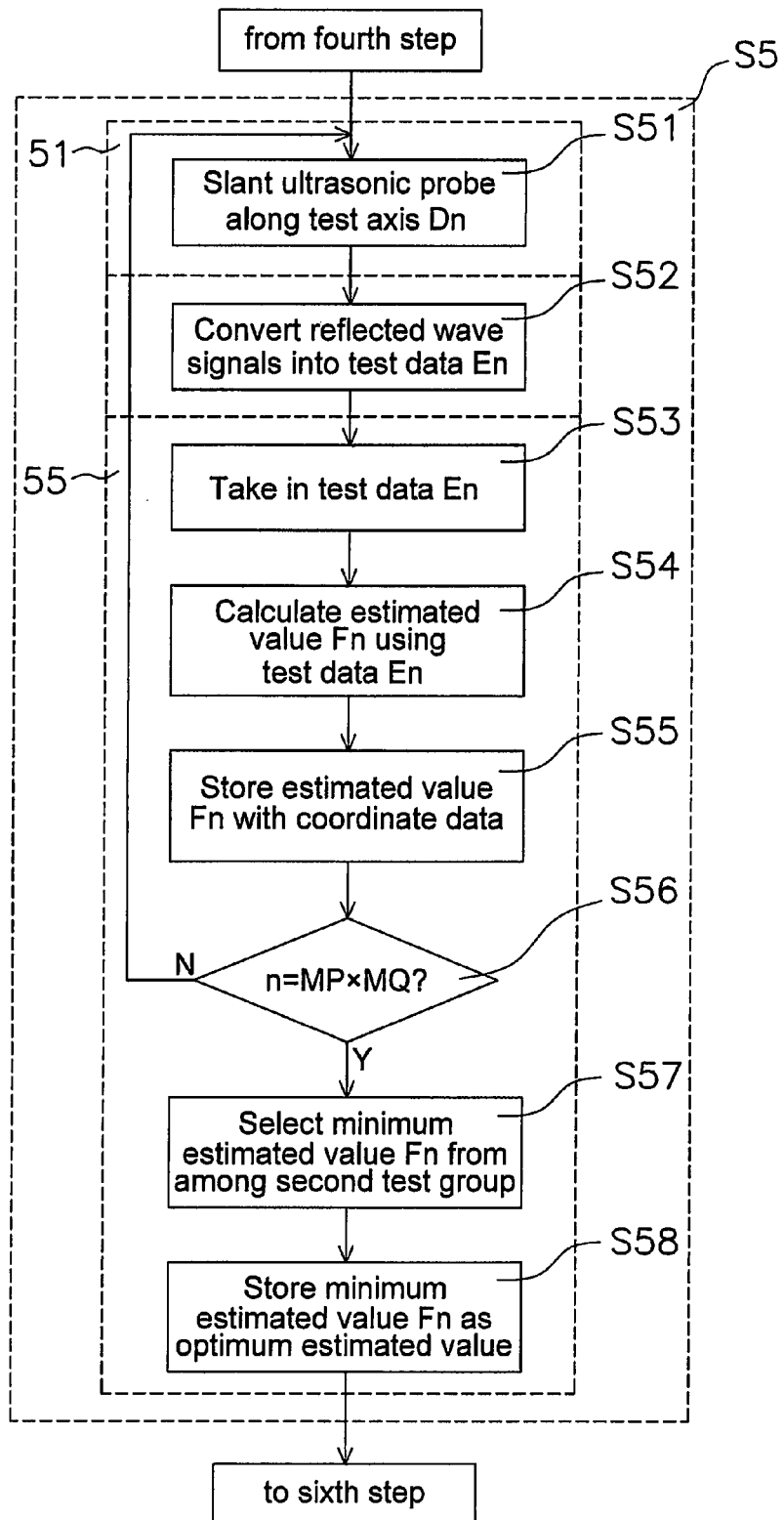
FIG. 10 is a detailed flow chart of the fifth step S5.

As shown in a flow diagram in FIG. 10, first, the ultrasonic probe 2a is moved by the robot arm 4 to the real center location, the tip of the ultrasonic probe 2a is brought into contact with the real center location (step S51). Next, the ultrasonic test instrument main device 2b obtains the test data with reference to the reflected wave detection signals sent from the ultrasonic probe 2a (step S52).

The test data $E_1$ at the test axis $D_1$ obtained by the ultrasonic test instrument main device 2b are taken into the control device 5 (step S53). Then, the estimated value computing unit of the control device 5 computes the estimated value $F_1$ using the test data $E_1$ (step S54). As an estimated value, one computed with the same calculating formula at the fifth step S5 is used. The calculated estimated value $F_1$ is stored by the optimum estimated value computing unit of the control device 5 into the control device 5 as a second group of the test data as well as the angle data of the test axis $D_1$ (step S55). Until the estimated values $F_1$ to $F_{25}$ of the test axes $D_1$ to $D_{25}$ are obtained, the steps S51 to S55 are repeated (step S56).

From among all of estimated values $F_1$ to $F_{25}$, the minimum estimated value $F_n$ is selected (step S57). Then, the selected minimum estimated value is stored into the control device 5 as an optimum estimated value (step S58).

As described above, at the fifth step S5, it is possible to obtain the optimum estimated value to check quality of the spot-welded portion.

(6) Sixth Step S6 (Determination Step)

At the sixth step S6, the quality of the spot-welded portion is checked by comparing the optimum estimated value obtained at the fifth step S5 and a criterion value gained by experiments. Specifically, if the optimum estimated value is equal to or less than the criterion value, it is determined that the quality of the welding of the spot-welded portion is good. If the optimum estimated value is larger than the criterion value, it is determined that the quality of the welding of the spot-welded portion is not good.

(7) Seventh Step S7 to Ninth Step S9

At the seventh step S7, test steps from the third step S3 to the sixth steps S6 are implemented on a plurality of spot-welded portions on one turbine shell 73. After the test is performed on all of the spot-welded portions at the seventh step S7, and at the eighth step S8, the ultrasonic probe 2a is removed so that the robot arm 4 can return the ultrasonic probe 2a to storage. Then, at the ninth step S9, the robot arm 4 discharges the turbine shell 73 to a corresponding position according to the judgment result at sixth step S6.

As described above, in the automatic ultrasonic examination device 1, unit provided in the tentative center location identifying device 6 and the control device 5 make it possible to check the quality of the spot-welded portions at high speed and with a high degree of accuracy compared to the operation by the operator.

3. Effects

The advantageous effect gained by the automatic ultrasonic examination device 1 and the examination method according to the present invention is summarized hereinafter.

In the automatic ultrasonic examination device 1, the real center location computing unit 54 of the control device 5 can identify the real center location of the spot-welded portion, i.e., the center location of the nugget 72, which cannot be judged from the appearance. The identifying of the center location which cannot be judged from the appearance makes it possible to check the quality of the spot-welded portion 70 with a high degree of accuracy at high speed compared to the test operation by the operator. Furthermore, the lattice arrangement of the test points $A_n$ makes it possible to identify precisely the real center location. Moreover, since the number of the test points $N_P$ and $N_Q$ or the spaces between the test points $\delta_P$ and $\delta_Q$ in the directions of P axis and Q axis are set by the initial setting unit 57, it is possible to deal with various spot-welded portions in size.

Furthermore, in the automatic ultrasonic examination device 1, the optimum estimated value computing unit 55 of the control device 5 selects an optimum estimated value from the second group of the test data along the test axes $D_n$. As a result, it is possible to obtain the better optimum estimated value to check the quality and to check the quality of the spot-welded portions with a high degree of accuracy compared to the operation by the operator.

In the automatic ultrasonic examination device 1, the tentative center location identifying device 6 can identify the tentative center location judging from the appearance. Accordingly, a range where the real center location computing unit 54 of the control device 5 obtains the first group of the test data can be set smaller, thereby making it possible to check the quality of the spot-welded portion with a high degree of accuracy at high speed.

Since the quality of the welded portion is checked by the above-described automatic ultrasonic examination device 1 and examination method, it is possible to check the quality of the welded portion with a high degree of accuracy at high speed, thereby improving the quality and productivity of the spot-welded products compared to the operation by the operator.

4. Other Embodiments

The present invention is not limited to the above-described embodiments, and it is possible to change or modify them variously without departing from a scope of the present invention. Hereinafter, a description will be made on other embodiments.

(1) Tentative Center Location Identifying Device 6

In the above-described embodiment, the tentative center location identifying device 6 identifies the center of the weld scar 71 in plane on the image. It is possible to identify three-dimensionally the tentative center location by an image processing software application that three-dimensionally performs an image processing, so that it is possible to identify more precisely the tentative center location (especially, in a direction perpendicular to the flat surface defined so as to include the spot-welded portions 70). In this case, the number of the camera 6a is not limited to one, i.e., a plurality of cameras 6a may be used.

In the above-described embodiment, the tentative center location identifying device 6 identifies the tentative center location. If the preset initial center location is very close to the tentative center location or setting of the number of the test points $N_p$ and $N_Q$ or the test spaces $\delta_p$ and $\delta_Q$ is adjusted so as to expand the test range at fifth step S5, it is unnecessary to use the tentative center location identifying device 6, making use of the initial center location as a tentative center location.

(2) Control Device 5

In the above-described embodiment, the ultrasonic test instrument main device 2b, the control device 5, and the image processing device 6b are different apparatuses. These functions are realized by a personal computer or the like into which software applications are installed that are provided with all functions of these apparatuses.

(3) Real Center Location Computing Unit 54

In the above-described embodiment, at the fourth step S4, the real center location computing unit 54 sets a plurality of test points into a lattice arrangement. It is possible not to employ the lattice arrangement but to set various positionings of the test points depending on other conditions such as size of the spot-welded portion.

(4) Optimum Estimated Value Computing Unit 55

In the above-described embodiment, the optimum estimated value computing unit 55 sets a plurality of test axes at the fifth step S5. It is possible to set the axes in different ways. For example, various settings of the test axes can be performed depending on accuracy or time, e.g., swinging the slanted ultrasonic probe 2a around the central axis at an angle to obtain estimated values. Depending on the product, the number of axes that are set can be decreased.

INDUSTRIAL APPLICABILITY

In the automatic ultrasonic examination device and the examination method according to the present invention, the above-described identification of the center location of the nugget and the estimate of the test points makes it possible to perform the test with a high degree of accuracy at high speed. Furthermore, in the production method according to the present invention, the use of the automatic ultrasonic examination method makes it possible to improve quality and productivity of the spot-welded products. Accordingly, the automatic ultrasonic examination device, the examination method, and the production method according to the present invention are useful in fields where it is required to perform the test with a high degree of accuracy at high speed or to improve quality and productivity of the spot-welded products.

The invention claimed is:

1. An automatic ultrasonic examination device to check automatically quality of a spot-welded portion of a test object, comprising:
    an ultrasonic test instrument including
        an ultrasonic probe to send ultrasonic waves and to detect reflected waves while being in contact with the spot-welded portion, the ultrasonic probe being configured to provide a plurality of estimated values indicating a state of the spot-welded portion with reference to pieces of test information obtained around a central axis of a real center location while pivoting on a contact point between the ultrasonic probe and the real center location, and
        an ultrasonic test instrument main device connected to the ultrasonic probe to convert reflected wave detection signals received from the ultrasonic probe into the test information;
    a robot arm including a plurality of joints to adjust three-dimensionally posture and location of the ultrasonic probe relative to the spot-welded portion; and
    a control device being connected to the ultrasonic test instrument and robot arm to communicate data and signals with the ultrasonic test instrument and robot arm,
    the control device including
        a real center location identifying unit to identify the real center location of the spot-welded portion with reference to pieces of test information obtained around a preset tentative center location of the spot-welded portion,
        an optimum estimated value computing unit causing the ultrasonic probe to pivot on the contact point around the central axis to obtain the plurality of estimated values, the optimum estimated value computing unit to select an optimum estimated value from the plurality of estimated values, and
        a determination unit to check quality of the spot-welded portion with reference to the optimum estimated value obtained by the optimum estimated value computing unit.

2. The automatic ultrasonic examination device according to claim 1, further comprising a tentative center location identifying unit connected to the control device to identify the tentative center location by taking in and image processing image data of the spot-welded portion.

3. The automatic ultrasonic examination device according to claim 1, wherein the location and number of test points corresponding to the test information are configured to be preset by the control device.

4. The automatic ultrasonic examination device according to claim 3, wherein a space between adjacent test points corresponding to the test information are configured to be preset by the control device.

5. The automatic ultrasonic examination device according to claim 4, wherein test points corresponding to the test information are located around the tentative center location in a lattice arrangement.

6. The automatic ultrasonic examination device according to claim 5, further comprising a tentative center location identifying unit connected to the control device to identify the tentative center location by taking in and image processing image data of the spot-welded portion.

7. An automatic ultrasonic examination method to check automatically quality of a spot-welded portion of a test object, in an automatic ultrasonic examination device including an ultrasonic test instrument to obtain test information from the test object, and a robot arm to adjust three-dimensionally posture and position of the ultrasonic test instrument relative to the test object, comprising:
- a real center location identifying step to identify a real center location of the spot-welded portion with reference to pieces of the test information around a tentative center location of the spot-welded portion obtained by the ultrasonic test instrument;
- an optimum estimated value computing step to obtain a plurality of estimated values indicating a state of the spot-welded portion with reference to pieces of test information obtained around a central axis of the real center location from an ultrasonic probe of the ultrasonic test instrument pivoting on a contact point between the ultrasonic probe and the real center location, the optimum estimated value computing step to select an optimum estimated value from the plurality of estimated values; and
- a determination step to check quality of the spot-welded portion with reference to the optimum estimated value obtained in the optimum estimated value computing step.

8. The automatic ultrasonic examination device according to claim 3, wherein test points corresponding to the test information are located around the tentative center location in a lattice arrangement.

9. The automatic ultrasonic examination method according to 7, further comprising a tentative center location identifying step to identify the tentative center location by image-processing image data of the spot-welded portion.

10. A method of producing spot-welded products, comprising,
- a spot welding step to spot-weld a plurality of metal materials; and
- an ultrasonic test step to check the quality of the welded portion of the spot-welded product using an ultrasonic examination method according to claim 7.

11. The automatic ultrasonic examination device according to claim 1, wherein a space between adjacent test points corresponding to the test information are configured to be preset by the control device.

12. The automatic ultrasonic examination device according to claim 11, wherein test points corresponding to the test information are located around the tentative center location in a lattice arrangement.

13. The automatic ultrasonic examination device according to claim 1, wherein test points corresponding to the test information are located around the tentative center location in a lattice arrangement.

* * * * *